United States Patent
Baird et al.

[11] 3,935,232
[45] Jan. 27, 1976

[54] PROCESS FOR MANUFACTURING HETEROCYCLIC COMPOUNDS

[75] Inventors: David Boyd Baird; Ronald Baker; Brian Ribbons Fishwick; Robert David McClelland, all of Manchester, England

[73] Assignee: Imperial Chemical Industries Limited, London, England

[22] Filed: Oct. 11, 1974

[21] Appl. No.: 514,319

Foreign Application Priority Data
June 9, 1972 United Kingdom............ 27005/72
Aug. 29, 1972 United Kingdom............ 39948/72

[52] U.S. Cl......................................... 260/332.2 C
[51] Int. Cl.²..................................... C07D 333/24
[58] Field of Search................ 260/332.2 C, 332.2 A

[56] References Cited
FOREIGN PATENTS OR APPLICATIONS
1,020,641 12/1957 Germany..................... 260/332.3 C

*Primary Examiner*—James O. Thomas, Jr.
*Assistant Examiner*—A. Siegel
*Attorney, Agent, or Firm*—Cushman, Darby & Cushman

[57] ABSTRACT

A process for the manufacture of the heterocyclic compounds of the formula:

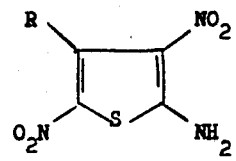

wherein R is a hydrogen atom or a hydrocarbon radical, which comprises decarboxylating and dinitrating a compound of the formula:

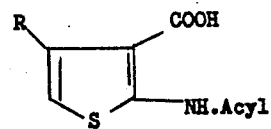

wherein R has the meaning stated above, and finally hydrolysing off the acyl group, and the use of the said heterocyclic compounds as diazo components in the production of azo dyestuffs.

1 Claim, No Drawings

PROCESS FOR MANUFACTURING HETEROCYCLIC COMPOUNDS

This is a division of application Ser. No. 363,818 filed May 25, 1973, now abandoned.

This invention relates to a process for manufacturing heterocyclic compounds of the thiophene series.

According to the invention there is provided a process for the manufacture of the heterocyclic compounds of the formula:

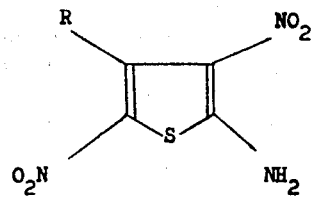

wherein R is a hydrogen atom or a hydrocarbon radical, which comprises decarboxylating and dinitrating a compound of the formula

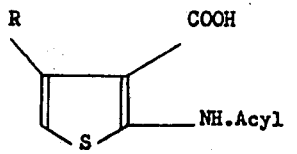     Formula I wherein R has the meaning stated above, and finally hydrolysing off the acyl group.

The hydrocarbon radicals represented by R are preferably alkyl radicals, in particular lower alkyl radicals containing from 1 to 4 carbon atoms such as methyl and ethyl radicals, cycloalkyl radicals such as cyclohexyl, aralkyl radicals in particular phenyl lower alkyl radicals such as benzyl and β-phenylethyl radicals, and aryl radicals, in particular monocyclic aryl radicals such as phenyl, tolyl and xylyl radicals. R is preferably alkyl and, above all, hydrogen.

As specific examples of the said acyl groups there may be mentioned formyl, acetyl, propionyl, benzoyl, methyl sulphonyl, chloroacetyl, β-carboxypropionyl and p-toluenesulphonyl. It is however preferred that the acyl group is of the formula -COX wherein X is a hydrogen atom or a lower alkyl radical.

In carrying out the process of the invention the compound of Formula I can be decarboxylated prior to the dinitration, or one nitro group can be introduced in the 5-position of the thiophene ring followed by decarboxylation and introduction of the nitro group into the 3-position or the dinitration can be carried out under such conditions that simultaneous decarboxylation takes place.

The decarboxylation of the compound of Formula I can be effected by heating the compound to a temperature above its melting point, or by heating it in a solvent at a temperature between 100° and 300°C, preferably in a basic solvent such as a secondary or tertiary aromatic amine at a temperature between 170° and 230°C or alternatively in a mixture of such a basic solvent and an inert solvent as kerosene. As examples of the said basic solvents there may be mentioned N-alkyl and N:N-dialkylanilines such as dimethylaniline, diethylaniline and ethylaniline and also quinoline. The subsequent dinitration can then be effected using nitric acid in a sulphuric acid medium which optionally contains free sulphur trioxide.

The simultaneous dinitration and decarboxylation of the compound of Formula I can be carried out by stirring the compound in a mixture of nitric acid (at least 2 mols per mole of the compound of Formula I) and sulphuric acid which may contain free sulphur trioxide or up to 25% by weight of water, preferably at a temperature between −20° and 30°C.

Nitration of the compound of Formula I to give the corresponding 5-nitro derivative can be effected by nitration in acetic anhydride medium but is preferably carried out in sulphuric acid medium at a temperature preferably below 0°C using 1 mol of nitric acid, the resulting compound then being decarboxylated by heat followed by nitration using a mixture of nitric acid and sulphuric acid.

The final hydrolysis of the acyl group can be effected by treating the dinitro compound with an aqueous or alcoholic solution of a mineral acid such as sulphuric acid preferably by heating to a temperature in the region of 100°C. It is not essential to isolate the dinitro compound prior to the hydrolysis since this can be effected by diluting the nitration mixture with the necessary amount of water, heating to hydrolyse off the acyl group and then isolating the resulting compound by conventional means; for example by further dilution with water, filtering off the solid which is precipitated. When the deacylation is carried out immediately after the nitration then it is preferred to add a substance such as sulphamic acid to destroy any nitrous acid or other oxidising agents present.

When R in the compound of Formula I represents an aralkyl or aryl radical, then the conditions necessary for the dinitration of the thiophene nucleus may additionally introduce a nitro group or groups into the aryl ring of, or present in, said radical represented by R. However, the production of such compounds also falls within the scope of the present invention.

The compounds of Formula I can themselves by obtained by treating a compound of the formula

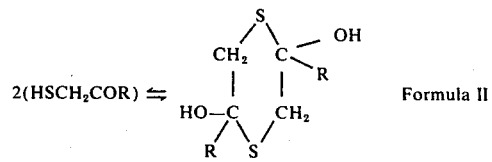     Formula II with cyanoacetic acid or an alkyl cyanoacetate such as ethyl cyanoacetate, or cyanoacetamide in aqueous alkaline medium optionally containing an aliphatic alcohol (for example an aqueous solution of sodium hydroxide) preferably at a temperature between 20° and 100°C. An acylating agent, for example acetic anhydride, is then added and the pH of the mixture is maintained between 4 and 10 preferably between 7 and 9 by the addition of alkali until the acylating is complete. If the acylating agent is an acid anhydride then control of the pH is not so essential provided that an excess of the anhydride is always present in the reaction mixture. The mixture is then acidified and the compound of Formula I which is precipitated is filtered off and dried.

As examples of acylating agents there may be mentioned acetyl chloride, chloroacetyl chloride, acetic anhydride, propionic anhydride, a mixture of formic acid and acetic anhydride, benzoyl chloride, p-toluene sulphonyl chloride, methane sulphonyl chloride, succinic anhydride and phthalic anhydride.

The compounds of Formula II can themselves be obtained by dimerisation of the corresponding mercaptoaldehyde or ketone of the formula $HS.CH_2COR$ prepared for example by reaction of the appropriate haloaldehyde or haloketone with sodium hydrosulphide in aqueous medium. If desired the subsequent reaction with the cyanoacetic acid can be carried out without isolating the compounds of Formula II.

The heterocyclic compounds obtained by the process of the invention are valuable as diazo components in the manufacture of disperse monoazo dyestuffs.

The invention is illustrated but not limited by the following Examples in which the parts and percentages are by weight.

EXAMPLE 1

A mixture of 5.55 parts of 2-acetylaminothiophene-3-carboxylic acid and 27 parts of sulphuric acid monohydrate is stirred at 0°C and a mixture of 10 parts of water, 30.4 parts of sulphuric acid and 7.0 parts of 80°Tw nitric acid is added dropwise, the temperature of the resulting mixture being maintained below 0°C by external cooling. The mixture is then poured into a solution of 10 parts of sodium acetate in 250 parts of water, the temperature being maintained between 45° and 60°C by the addition of ice, and the pH being maintained at 4 by the addition of a concentrated aqueous solution of sodium hydroxide. The mixture is stirred for 30 minutes at 50°C, then cooled to 25°C and the precipitated 2-acetylamino-3:5-dinitrothiophene is filtered off, washed with water and dried. The yield is 2.6 parts (37.5%).

A mixture of 5 parts of 2-acetylamino-3:5-dinitrothiophene, 92 parts of sulphuric acid and 50 parts of water is stirred for 3 hours at 90°C. The mixture is then poured onto 150 parts of ice, and the precipitated 2-amino-3:5-dinitrothiophene is filtered off, washed with water and dried. The yield is 3.6 parts (88%).

The 2-acetylaminothiophene-3-carboxylic acid used in the above Example was itself obtained as follows:

46.5 Parts of cyanoacetic acid were added to a mixture of 50 parts of a 70°Tw aqueous solution of sodium hydroxide and 180 parts of water, followed by 38 parts of mercaptoacetaldehyde dimer. The resulting mixture was then heated for 5 minutes at 80°C after which it was cooled to 20°C. 100 Parts of acetic anhydride were added during 15 minutes, the pH of the mixture being maintained between 6 and 7 by the addition of an aqueous solution of sodium hydroxide. The mixture was then filtered, the filtrates acidified with an aqueous solution of hydrochloric acid, and the precipitated solid filtered off, washed with water and dried. The product was obtained in a yield of 90%, and had a melting point of 216° – 217°C.

EXAMPLE 2

A mixture of 18.5 parts of 2-acetylaminothiophene-3-carboxylic acid and 76.5 parts of N:N-dimethylaniline is stirred for 1 hour at 195°C. The mixture is cooled to 25°C, 200 parts of water added, and the N:N-dimethylaniline removed by distillation in the presence of steam. The aqueous residue is filtered hot, the filtrate cooled to 20°C and the 2-acetylaminothiophene which crystallises out is filtered off and dried. The yield is 70.2%, and the product melts at 160° to 161°C.

4.23 parts of the 2-acetylaminothiophene are added during 30 minutes to a mixture of 46 parts of sulphuric acid monohydrate and 4.05 parts of 100°Tw nitric acid, the temperature of the mixture being maintained between −5° and 0°C by external cooling. The mixture is then stirred for 30 minutes at the same temperature, poured into a mixture of 125 parts of water and 125 parts of ice, and the precipitated 2-acetylamino-3:5-dinitrothiophene filtered off, washed with water and dried. The yield is 76.5% and the product melts at 178° to 180°C.

A mixture of 5 parts of the 2-acetylamino-3:5-dinitrothiophene, 92 parts of sulphuric acid and 50 parts of water is stirred for 3 hours at 90°C. The mixture is poured into 150 parts of ice, and the precipitated 2-amino-3:5-dinitrothiophene is filtered off, washed with water and dried. The yield is 88% and the product melts at 170°C with decomposition.

The 2-acetylaminothiophene-3-carboxylic acid used in this Example was obtained as follows:

117 parts of cyanoacetic acid were added to a mixture of 236 parts of a 70°Tw. aqueous solution of sodium hydroxide and 450 parts of water, followed by 95 parts of 2:5-dihydroxy-1:4-dithiane. The mixture was stirred for 2 hours at 65° to 75°C, cooled to 20°C, then 270 parts of acetic anhydride added during 45 minutes the pH of the mixture being maintained between 7.5 and 9 by the gradual addition of 432 parts of a 70°Tw. aqueous solution of sodium hydroxide, and the temperature being maintained between 20° and 40°C. The mixture was then acidified with an aqueous solution of hydrochloric acid, and the precipitated 2-acetylaminothiophene-3-carboxylic acid filtered off, washed with water and dried. The yield was 90%.

The 2:5-dihydroxy-1:4-dithiane was itself obtained by slowly adding 172 parts of a 45% aqueous solution of chloroacetaldehyde to 200 parts of a 5M aqueous solution of sodium hydrosulphide at 0°–5°C, stirring for 2 hours at this temperature and then filtering off the precipitated product. The yield is 81% and the product melted at 127°–128°C.

In place of the 117 parts of cyanoacetic acid used above there were used 139 parts of ethyl cyanoacetate or 116 parts of cyanoacetamide whereby there was obtained in each case a 70% yield of 2-acetylaminothiophene-3-carboxylic acid.

EXAMPLE 3

The procedure of the first paragraph of Example 2 is repeated except that the 76.5 parts of N:N-dimethylaniline is replaced by 76.5 parts of N-ethylaniline or by 76.5 parts of quinoline. The yield of the resulting 2-acetylaminothiophene is respectively 82.3% and 71%, which is then converted to 2-amino-3:5-dinitrothiophene as described in Example 2.

EXAMPLE 4

The procedure of the first paragraph of Example 2 is repeated except that the 76.5 parts of N:N-dimethylaniline are replaced by a mixture of 50 parts of kerosene and 30 parts of dimethylaniline and the decarboxylation is carried out for 3 hours at 195°C. After crystallisation from aqueous ethanol a 55% yield of 2-acetylaminothiophene is obtained which is then converted to 2-amino-3:5-dinitrothiophene as described in Example 2.

Alternatively the decarboxylation is carried out by heating the 2-acetylaminothiophene-3-carboxylic acid for 10 minutes at 230°C in an atmosphere of nitrogen. After crystallisation from aqueous ethanol the resulting 2-acetylaminothiophene is converted to 2-amino-3:5-dinitrothiophene as described in Example 2.

EXAMPLE 5

51.3 parts of 2-formylaminothiophene-3-carboxylic acid are added to 500 parts of sulphuric acid (sp.gr. 1.84) at a temperature below 10°C, and 56.7 parts of a nitrating mixture (obtained by mixing together 633 parts of 20% oleum and 348 parts of nitric acid of sp.gr. 1.50) are then slowly added, the temperature of the mixture being maintained at −10° to −5°C by external cooling. The mixture is stirred for 5 minutes at −5°C, poured into an ice/water mixture and the precipitated 2-formylamino-5-nitrothiophene-3-carboxylic acid (90% yield) is filtered off, washed with water and dried.

10.8 parts of the 2-formylamino-5-nitrothiophene-3-carboxylic acid are dissolved in 100 parts of sulphuric acid (sp.gr. 1.84) and 9.45 parts of the above nitrating mixture are slowly added at −5° to 0°C. The mixture is stirred for 1 hour at the same temperature, poured onto ice and the precipitated 2-formylamino-3:5-dinitrothiophene (m.pt. 186°–188°C; yield 8.1 parts) isolated. Treatment of this product in a hot 4% ethanol solution of sulphuric acid gives 2-amino-3:5-dinitrothiophene in 85% yield.

The 2-formylaminothiophene-3-carboxylic acid was itself obtained as follows:

46.5 parts of cyanoacetic acid were added to a mixture of 50 parts of a 70°Tw aqueous solution of sodium hydroxide and 18 parts of water followed by 38 parts of mercaptoacetaldehyde dimer. The mixture was stirred for 24 hours at 20°C and then slowly added to a mixture of 150 parts of formic acid and 150 parts of acetic anhydride which had been previously stirred together for 1 hour at 20°C and then cooled to 5°C, the temperature of the resulting mixture being maintained at 5°–10°C. The mixture was stirred for 1 hour, acidified with an aqueous solution of hydrochloric acid to pH 3 and the precipitated 2-formylaminothiophene-3-carboxylic acid (m.p. 244°C, yield 75%) filtered off, washed with water and dried.

EXAMPLE 6

By replacing the 51.3 parts of 2-formylaminothiophene-3-carboxylic acid used in the first paragraph of Example 5 by an equivalent amount of 2-acetylaminothiophene-3-carboxylic acid, 2-acetylamino-5-nitrothiophene-3-carboxylic acid (m.pt. 238°–240°C) is obtained in 80% yield. This on subsequent heating in the presence of benzoic acid gives 2-acetylamino-5-nitrothiophene (m.pt. 226°C) which on subsequent nitration is sulphuric acid medium at 0°C, followed by hydrolysis, gives 2-amino-3:5-dinitrothiophene.

EXAMPLE 7

11.1 parts of 2-acetylaminothiophene-3-carboxylic acid are dissolved in 55 parts of sulphuric acid at 10°–20°C. The solution is cooled to 0°C, and 28 parts of the nitrating mixture described in Example 5 gradually added whilst the temperature is maintained at −5° to 0°C by external cooling. The mixture is stirred for 30 minutes, poured into ice and the precipitated 2-acetylamino-3:5-dinitrothiophene filtered off, washed with water, then with an aqueous solution of sodium acetate and dried. The N-acetyl group is then removed by heating in a hot aqueous solution of hydrochloric acid to give 2-amino-3:5-dinitrothiophene in an overall yield of 40%.

EXAMPLE 8

In place of the 11.1 parts of 2-acetylaminothiophene used in Example 7 there are used 11.9 parts of 2-acetylamino-4-methylthiophene-3-carboxylic acid whereby 2-amino-4-methyl-3:5-dinitrothiophene (m.pt. 157°–159°C) is obtained.

The 2-acetylamino-4-methylthiophene-3-carboxylic acid was itself obtained as follows:

92.5 parts of chloroacetone were gradually added to 210 parts of a 5M aqueous solution of sodium hydrosulphite, the temperature being maintained at 0° to 2°C by external cooling. 120 parts of an aqueous solution of sodium hydroxide of sp.gr. 1.35 and 93 parts of cyanoacetic acid were then added, and the mixture stirred for 2 hours at 60°C. The mixture was filtered, cooled to 0°–10°C and 200 parts of acetic anhydride added, the pH of the mixture being maintained between 7.5 and 9 by the simultaneous addition of sodium hydroxide, and the temperature being maintained between 5° and 10°C. The mixture was then filtered, the filtrate acidified with hydrochloric acid, and the precipitated 2-acetylamino-4-methylthiophene-3-carboxylic acid (m.pt. 234°C, yield 81%) was filtered off, washed with water and dried.

EXAMPLE 9

A mixture of 5 parts of 2-acetylamino-4-methylthiophene-3-carboxylic acid and 50 parts of N:N-diethylaniline is heated for 20 minutes at the boil. The mixture is cooled, 100 parts of a light petroleum ether added, and the precipitated 2-acetylamino-4-methylthiophene (81% yield) filtered off and dried.

The 2-acetylamino-4-methylthiophene is dinitrated and deacetylated by the method described in Example 2 above giving 2-amino-4-methyl-3:5-dinitrothiophene.

EXAMPLE 10

A mixture of 9 parts of 2-acetylamino-4-phenylthiophene-3-carboxylic acid and 27 parts of N:N-diethylaniline is heated for 45 minutes at the boil. The mixture is cooled, 30 parts of a light petroleum fraction added and the 2-acetylamino-4-phenylthiophene (m.pt. 184°C) filtered off. The 2-acetylamino-4-phenylthiophene is then dinitrated and de-acetylated by the process described in Example 2, to give 2-amino-3:5-dinitro-4-phenylthiophene.

The 2-acetylamino-4-phenylthiophene-3-carboxylic acid was itself obtained by acetylation of 2-amino-3-ethoxycarbonyl-4-phenylthiophene followed by hydrolysis of the ester group with an aqueous solution of sodium hydroxide.

EXAMPLE 11

51.3 parts of 2-formylaminothiophene-3-carboxylic acid are added to 500 parts of sulphuric acid (sp.gr. 1.84) at a temperature between 5° and 10°C, and 113.4 parts of the nitrating mixture described in Example 5 are then added at a temperature between −10° and −5°C. The mixture is then stirred for 1 hour at −5°C to 0°C and the mixture poured into 650 parts of ice and 250 parts of water containing 20 parts of sulphamic acid. The mixture is heated for 6 hours at 60°C, cooled and the precipitated 2-amino-3:5-dinitrothiophene filtered off, washed with water and dried.

EXAMPLE 12

In place of the 51.3 parts of 2-formylaminothiophene-3-carboxylic acid used in Example 11 there are used equivalent amounts of 2-(β-carboxypropionylamino)thiophene-3-carboxylic acid or 2-(chloroacetylamino)thiophene-3-carboxylic acid when 2-amino-3:5-dinitrothiophene is similarly obtained.

The 2-(β-carboxypropionylamino)thiophene-3-carboxylic acid was obtained as follows:

51.5 parts of an aqueous solution of sodium hydroxide of sp.gr. 1.35 was added, at a temperature below 20°C, to a solution of 26.4 parts of cyanoacetic acid in 102 parts of water, 21.5 parts of mercaptoacetaldehyde dimer were then added and the mixture stirred for 3 hours at 60°–70°C. The solution was then cooled to 5°C, 38 parts of succinic anhydride added at a temperature below 40°C, the pH of the mixture being maintained between 7.5 and 10 by the addition of sodium hydroxide. The pH was then adjusted to 7, the mixture filtered, the filtrate acidified and the solid (m.pt. 200°–202°C (dec); yield 85%) filtered off, washed with water and dried.

The 2-(chloroacetylamino)thiophene-3-carboxylic acid was prepared in similar manner, the succinic anhydride being replaced by an equivalent amount of chloroacetyl chloride and the acylation being carried out at a temperature below 10°C.

EXAMPLE 13

5.55 parts of 2-acetylaminothiophene-3-carboxylic acid and a mixture of 20 parts of 20% oleum and 4 parts of nitric acid of sp.gr. 1.50 are simultaneously added to 30 parts of sulphuric acid monohydrate, the temperature of the mixture being maintained at −5° to 0°C by external cooling. The mixture is then stirred for 1 hour at the same temperature, poured into a mixture of ice and water and the precipitated 2-acetylamino-3:5-dinitrothiophene filtered off, washed with water and dried. The product is then de-acetylated as previously described to give 2-amino-3:5-dinitrothiophene.

EXAMPLE 14

A mixture of 10 parts of acetic acid, 10 parts of acetic anhydride and 1.89 parts of nitric acid of sp.gr. 1.50 is added to a suspension of 5.55 parts of 2-acetylaminothiophene-3-carboxylic acid in 35 parts of acetic anhydride, the temperature of the mixture being maintained at 20° to 25°C. The mixture is stirred for 2 hours at the same temperature, poured into a mixture of ice and water and the precipitated 2-acetylamino-5-nitrothiophene-3-carboxylic acid (m.pt. 233°–237°C) filtered off, washed with water and dried. On decarboxylation and nitration as described above the product is converted to 2-amino-3:5-dinitrothiophene.

We claim:
1. A process for the manufacture of a compound of the formula

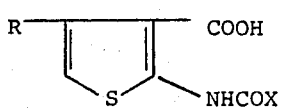

wherein R is selected from the group consisting of hydrogen, lower alkyl and phenyl and X is selected from the group consisting of hydrogen, lower alkyl, chloromethyl and β-carboxyethyl, which comprises reacting a compound of the formula HSCH₂OR or a dimer thereof having the formula

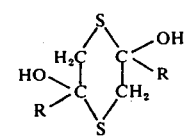

wherein R has the meaning given above, with cyanoacetic acid, lower alkyl cyanoacetate or cyanoacetamide in an aqueous alkaline medium at a temperature between 20° and 100°C, adding an acylating agent of an acid of the formula HOOCX wherein X has the meaning given above and acylating at a pH of between 4 and 10 by addition, as necessary, of an aqueous solution of an alkali.

* * * * *